(12) United States Patent
Katakura (10) Patent No.: US 9,684,152 B2
(45) Date of Patent: Jun. 20, 2017

(54) ENDOSCOPE OBJECTIVE OPTICAL SYSTEM

(71) Applicant: OLYMPUS CORPORATION, Tokyo (JP)

(72) Inventor: Masahiro Katakura, Tokyo (JP)

(73) Assignee: OLYMPUS CORPORATION, Tokyo (JP)

(*) Notice: Subject to any disclaimer, the term of this patent is extended or adjusted under 35 U.S.C. 154(b) by 0 days.

(21) Appl. No.: 14/264,704

(22) Filed: Apr. 29, 2014

(65) Prior Publication Data
US 2014/0307329 A1   Oct. 16, 2014

Related U.S. Application Data

(63) Continuation of application No. PCT/JP2013/074768, filed on Sep. 12, 2013.

(30) Foreign Application Priority Data
Oct. 2, 2012  (JP) ................................. 2012-220596

(51) Int. Cl.
*G02B 13/04* (2006.01)
*A61B 1/00* (2006.01)
(Continued)

(52) U.S. Cl.
CPC .......... *G02B 13/04* (2013.01); *A61B 1/00096* (2013.01); *A61B 1/00188* (2013.01);
(Continued)

(58) Field of Classification Search
CPC ............ A61B 1/00163; A61B 1/00174; A61B 1/00188; A61B 1/00177; A61B 1/00096;
(Continued)

(56) References Cited

U.S. PATENT DOCUMENTS

2005/0225872 A1* 10/2005 Uzawa et al. ................ 359/661
2006/0274433 A1   12/2006 Kamo
(Continued)

FOREIGN PATENT DOCUMENTS

JP  2006-337690   12/2006
JP  2007-025499   2/2007
(Continued)

OTHER PUBLICATIONS

Machine translation of JP 2012-047909 (Mizusawa Masayuki) Mar. 8, 2012[retrieved on Nov. 8, 2014] Retrieved from AIPN Japan Patent Office.*
(Continued)

*Primary Examiner* — Thomas K Pham
*Assistant Examiner* — Cara Rakowski
(74) *Attorney, Agent, or Firm* — Andrews Kurth Kenyon LLP

(57) ABSTRACT

To off-axis and on-axis aberrations at low cost while having a wide angle of view, an endoscope objective optical system (1) has in order: a negative first lens (L1); a negative second lens (L2) and a third lens (L3) joined to each other; a brightness diaphragm (S); and a positive lens group (G2) having a cemented lens (CL2) including one positive lens and one negative lens joined to each other, and satisfies expressions (1) and (2):

$$1.0 < D3(96\ deg)/f\_all < 10 \quad (1)$$

$$1.1 < (r1+r2)/(r1-r2) < 5.0 \quad (2)$$

where, D3(96 deg) is a distance in which a chief ray of a d-line having an incident angle of 96 degrees that enters the first lens transmits the third lens, f_all is a focal distance of the whole system, r1 and r2 are radii of
(Continued)

curvature of an object side surface of the first lens and an image side surface of the second lens, respectively.

4 Claims, 9 Drawing Sheets

(51) Int. Cl.
*G02B 23/24* (2006.01)
*G02B 9/04* (2006.01)
*G02B 13/00* (2006.01)
*G02B 9/10* (2006.01)

(52) U.S. Cl.
CPC .............. *G02B 23/243* (2013.01); *G02B 9/04* (2013.01); *G02B 9/10* (2013.01); *G02B 13/005* (2013.01)

(58) Field of Classification Search
CPC .... G02B 23/243; G02B 23/2438; G02B 9/04; G02B 9/62; G02B 9/64; G02B 13/0045; G02B 13/004; G02B 13/005
USPC ................ 359/664, 740, 762, 761, 749–753, 359/648–651, 656–661, 682, 691, 781, 359/771, 754, 793
See application file for complete search history.

(56) References Cited

U.S. PATENT DOCUMENTS

| | | | |
|---|---|---|---|
| 2007/0206295 A1 | 9/2007 | Yamashita et al. | |
| 2009/0278920 A1 | 11/2009 | Kamo | |
| 2010/0188757 A1 | 7/2010 | Saitoh | |
| 2010/0254025 A1 | 10/2010 | Yoshida et al. | |
| 2011/0164324 A1* | 7/2011 | Okumura ...................... | 359/682 |
| 2012/0099211 A1* | 4/2012 | Peng et al. .................... | 359/753 |
| 2012/0170142 A1* | 7/2012 | Hsieh et al. .................. | 359/762 |

FOREIGN PATENT DOCUMENTS

| | | |
|---|---|---|
| JP | 2007-233152 | 9/2007 |
| JP | 2008-058387 | 3/2008 |
| JP | 2009-063877 | 3/2009 |
| JP | 2009-276371 | 11/2009 |
| JP | 2010-243711 | 10/2010 |
| JP | 2011-227380 | 11/2011 |
| JP | 2012-047909 | 3/2012 |
| WO | 2009/066532 | 5/2009 |

OTHER PUBLICATIONS

International Search Report, dated Dec. 10, 2013, issued in corresponding International Application No. PCT/JP2013/074768.

* cited by examiner

ENDOSCOPE OBJECTIVE OPTICAL SYSTEM

TECHNICAL FIELD

The present invention relates to a wide-angle endoscope objective optical system applied to an endoscope apparatus.

BACKGROUND ART

A sufficient angle of view is required for an objective optical system applied to an endoscope apparatus. As such wide-angle objective optical systems applicable to endoscopes, for example, in PTLs 1 to 4, disclosed are endoscope objective optical systems in each of which is provided: a negative first lens; a negative second lens; a positive third lens; a brightness diaphragm; and a positive lens group from an object side, and in each of which an angle of view is set to be not less than 200 degrees while suppressing a lens diameter. In each of these endoscope objective optical systems, the first lens closest to the object side has a convex meniscus shape, and thus distortion is successfully corrected although the lens has a wide angle.

CITATION LIST

Patent Literature

{PTL 1}
Japanese Unexamined Patent Application, Publication No. 2012-47909
{PTL 2}
Japanese Unexamined Patent Application, Publication No. 2011-227380
{PTL 3}
Japanese Unexamined Patent Application, Publication No. 2007-25499
{PTL 4}
PCT International Publication No. WO 2009/066532

SUMMARY OF INVENTION

Technical Problem

However, in the above-described endoscope objective optical system disclosed in each PTL, there is a problem that an off-axis aberration is not successfully corrected because of a thin thickness of the third lens, and on-axis and off-axis aberrations are corrected using an aspherical lens, thus resulting in high lens cost.

The present invention has been made in view of the above-mentioned circumstances, and an object thereof is to provide an endoscope objective optical system that can successfully correct off-axis and on-axis aberrations at low cost while having a wide angle of view.

Solution to Problem

In order to achieve the above-described object, the present invention provides the following solutions.

One aspect of the present invention provides an endoscope objective optical system provided with: a first lens having negative optical power; a second lens having negative optical power; a third lens having positive optical power; a brightness diaphragm; and a lens group having positive optical power in order from an object side to an image side, in which the second and third lenses are joined to each other, the lens group has a cemented lens in which at least one positive lens and one negative lens have been joined to each other, and the following conditional expressions (1) and (2) are satisfied:

$$1.0 < D3(96 \text{ deg})/f\_all < 10 \quad (1)$$

$$1.1 < (r1+r2)/(r1-r2) < 5.0 \quad (2)$$

where, D3(96 deg) is a distance in which a chief ray of a d-line having an incident angle of 96 degrees that enters the first lens transmits the third lens, and f_all is a focal distance of the whole system.

In addition, r1 is a radius of curvature of an object side surface of a first lens L1, and r2 is a radius of curvature of an image side surface of a second lens L2.

DESCRIPTION OF EMBODIMENTS

Hereinafter, with reference to drawings, will be explained an endoscope objective optical system pertaining to one embodiment of the present invention.

Figure 1:
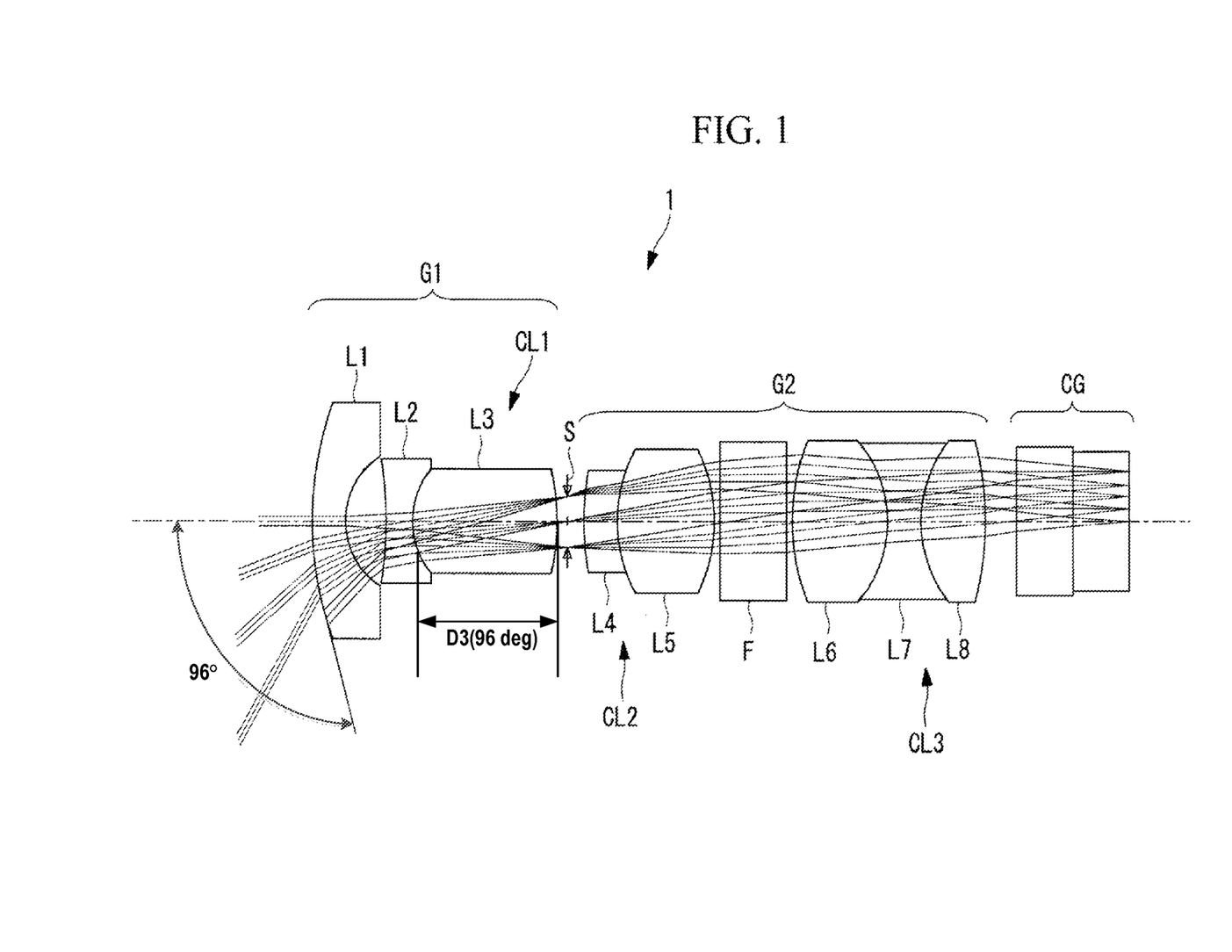
FIG. 1 is a cross-sectional diagram showing an overall configuration of an endoscope objective optical system pertaining to one embodiment of the present invention.

FIG. 1 shows a cross-sectional diagram showing an overall configuration of an endoscope objective optical system 1 pertaining to the present embodiment. As shown in FIG. 1, the endoscope objective optical system 1 is provided with: a negative lens group G1; a brightness diaphragm S; and a positive lens group G2 in order from an object side.

The negative lens group G1 has: a negative first lens L1; a negative second lens L2; and a positive third lens L3 in order from the object side. Among these, the negative second lens L2 and the positive third lens L3 are joined to each other to be a cemented lens CL1.

The positive lens group G2 has: a cemented lens CL2 in which a negative fourth lens L4 and a positive fifth lens L5 have been joined to each other; a plane-parallel plate F; and a cemented lens CL3 in which a positive sixth lens L6, a negative seventh lens L7, and a positive eighth lens L8 have been joined to each other.

Additionally, an imaging element, which is not shown, is arranged near an image surface of the endoscope objective optical system 1, and is included in the endoscope objective optical system and an imaging optical system. A cover glass CG for protecting an imaging surface is stuck on the imaging element.

Here, the endoscope objective optical system 1 is configured so as to satisfy the following conditional expressions:

$$1.0 < D3(96\ \text{deg})/f\_\text{all} < 10 \quad (1)$$

$$1.1 < (r1+r2)/(r1-r2) < 5.0 \quad (2)$$

where, D3(96 deg) is a distance in which a chief ray having an incident angle of 96 degrees that enters a first lens surface transmits a third lens surface, and f_all is a focal distance of the whole system.

In addition, r1 is a radius of curvature of an object side surface of the first lens L1, and r2 is a radius of curvature of an image side surface of the second lens L2.

A conditional expression (1) is a relational expression of a distance in which the chief ray of the d-line having the incident angle of 96 degrees that enters the first lens surface transmits the third lens surface, and the focal distance of the whole system. By satisfying the conditional expression (1), the third lens L3 can be set to have an appropriate lens thickness although having the angle of view of approximately 200 degrees, and an off-axis aberration can be successfully corrected. When D3(96 deg) falls below a lower limit of the conditional expression (1), the off-axis aberration cannot be successfully corrected, and meanwhile, when f_all exceeds an upper limit of the conditional expression (1), a trouble occurs that the brightness diaphragm S moves to an image side too much, an entrance pupil moves to an image surface side, and that a diameter of the first lens becomes too large.

A conditional expression (2) is the conditional expression concerning a shape factor of the first lens L1 of the negative lens group G1. By satisfying the conditional expression (2), required negative power can be obtained although the first lens L1 has a wide angle of view. When (r1+r2) falls below a lower limit of the conditional expression (2), refractive power of the negative first lens L1 decreases, and meanwhile, when (r1−r2) exceeds an upper limit of the conditional expression (2), a trouble occurs that productivity of each lens is significantly deteriorated.

Note that it is preferable to satisfy the following conditional expressions (1)' and (2)' instead of the above-described conditional expressions (1) and (2):

$$1.5 < D3(96\ \text{deg})/f\_\text{all} < 7 \quad (1)'$$

$$1.2 < (r1+r2)/(r1-r2) < 3.0 \quad (2)'$$

Furthermore, it is preferable to satisfy the following conditional expressions (1)'' and (2)'' instead of the above-described conditional expressions (1) and (2) or the conditional expressions (1)' and (2)':

$$1.7 < D3(96\ \text{deg})/f\_\text{all} < 5 \quad (1)''$$

$$1.3 < (r1+r2)/(r1-r2) < 1.7 \quad (2)''$$

In addition, it is preferable that the endoscope objective optical system 1 is configured so as to satisfy the following conditional expression (3):

$$51 < |v2-v3| < 60 \quad (3)$$

where, |v2−v3| is an absolute value of a difference between Abbe numbers of the second and third lenses.

The above-described conditional expression (3) is the conditional expression concerning the Abbe numbers of the negative second lens L2 and the positive third lens L3, and an appropriate difference between the Abbe numbers can be maintained by satisfying the conditional expression (3), thus enabling to successfully correct on-axis and off-axis chromatic aberrations. When |v2−v3| falls below a lower limit of the conditional expression (3), it becomes difficult to correct the on-axis and off-axis chromatic aberrations because of a small difference between the Abbe numbers, and meanwhile, when |v2−v3| exceeds an upper limit of the conditional expression (3), a problem arises that such combined lenses are significantly difficult to obtain, and that cost is high.

In addition, it is preferable that the endoscope objective optical system 1 is configured so as to satisfy the following conditional expression (4):

$$1.7 < Nd1 < 2.42 \quad (4)$$

where, Nd1 is a refractive index of the d-line of the first lens.

In addition, it is more preferable to satisfy the following conditional expression (4)' instead of the conditional expression (4), and further, it is still more preferable to satisfy a conditional expression (4)'' instead of the conditional expression (4) or (4)':

$$1.8 < Nd1 < 2.41 \quad (4)'$$

$$1.85 < Nd1 < 2.4 \quad (4)''$$

The above-described conditional expressions (4), (4)', and (4)'' are the conditional expressions concerning the refractive index of the negative first lens, a proper refractive index can be maintained by satisfying the conditional expression (4), and even though a curvature of the object side of the negative first lens L1 does not become extremely strong, appropriate negative power can be obtained. When Nd1 falls below a lower limit of the conditional expression (4), the extremely strong curvature must be given to the negative first lens L1, and the off-axis aberration is likely to occur, and meanwhile, when Nd1 exceeds an upper limit of the conditional expression (4), a problem arises that the lens itself becomes significantly difficult to obtain, and that cost increases.

Furthermore, it is preferable that the endoscope objective optical system 1 is configured so as to satisfy the following conditional expression (5):

$$1.7 < Nd2 < 2.42 \quad (5)$$

where, Nd2 is a refractive index of a d-line of the second lens.

In addition, it is more preferable to satisfy the following conditional expression (5)' instead of the conditional expression (5), and further, it is still more preferable to satisfy a conditional expression (5)" instead of the conditional expression (5) or (5)':

$$1.8<Nd2<2.41 \quad (5)'$$

$$1.85<Nd2<2.4 \quad (5)''$$

The above-described conditional expressions (5), (5)', and (5)' are the conditional expressions concerning a refractive index of the negative second lens, a proper refractive index can be maintained by satisfying the conditional expression (5), and even though a curvature of the object side of the negative second lens L2 does not become extremely strong, appropriate negative power can be obtained. When Nd2 falls below a lower limit of the conditional expression (5), the extremely strong curvature must be given to the negative second lens L2, and the off-axis aberration is likely to occur, and meanwhile, when Nd2 exceeds an upper limit of the conditional expression (5), a problem arises that the lens itself becomes significantly difficult to obtain, and that cost increases.

Furthermore, when power of the negative first lens L1 is set as PW_f1, and power of the cemented lens CL1 in which the negative second lens L2 and the positive third lens L3 have been joined to each other is set as PW_f2, it is preferable that the endoscope objective optical system 1 is configured so as to satisfy the following conditional expression (6):

$$0.3<PW\_1/PW\_2<2.0 \quad (6)$$

In addition, it is more preferable to satisfy the following conditional expression (6)' instead of the conditional expression (6), and further, it is still more preferable to satisfy a conditional expression (6)" instead of the conditional expression (6) or (6)":

$$0.5<PW\_1/PW\_2<1.7 \quad (6)'$$

$$0.8<PW\_1/PW\_2<1.5 \quad (6)''$$

The above-described conditional expression (6) is the conditional expression concerning power arrangement of the negative lens group G1. Since appropriate power arrangement can be achieved by satisfying the conditional expression (6), a lens diameter can be kept small while keeping the wide angle of view. When PW_2 exceeds an upper limit of the conditional expression (6), the power of the first lens L1 becomes too strong, and not only the wide angle of view cannot be kept but particularly the off-axis aberration is likely to occur, so that it is not preferable that PW_2 exceeds the upper limit. Meanwhile, when PW_1 falls below a lower limit of the conditional expression (6), the power of the second lens L2 becomes too strong, and thus a problem arises that the off-axis aberration is likely to occur, which also leading to enlargement of the first lens L1.

It is to be noted that the respective lenses included in the endoscope objective optical system pertaining to the present embodiment are all configured with spherical lenses, and that thereby increase in cost can be suppressed.

According to the endoscope objective optical system 1 pertaining to the present embodiment configured as described above, since the number of included lenses of each group can be reduced by arranging the negative lens group G1, the brightness diaphragm S, and the positive lens group G2 in order from the object side, an entire length of the endoscope objective optical system 1 can be shortened, and cost can be reduced. In addition, the diameter of the first lens L1 can be kept small. Furthermore, the on-axis and off-axis aberrations can be successfully corrected without using an aspherical lens by applying the cemented lens CL2 or CL3 to the positive lens group G2, and cost can be reduced.

In addition, since by configuring the cemented lens in which the negative second lens and the positive third lens have been joined to each other, the on-axis and off-axis chromatic aberrations can be successfully corrected, and a lens interval between the negative second lens and the positive third lens can be eliminated, an entrance pupil position can be moved to the object side, and the diameter of the first lens can be kept small.

EXAMPLE

Subsequently, with reference to FIGS. 2 to 9, will be explained Examples 1 to 4 of the endoscope objective optical system pertaining to the above-mentioned embodiment. In lens data described in each Example, r indicates a radius of curvature (a unit is mm), d indicates surface spacing (mm), Nd indicates a refractive index to the d-line, and Vd indicates an Abbe number to the d-line.

Example 1

Figure 2:
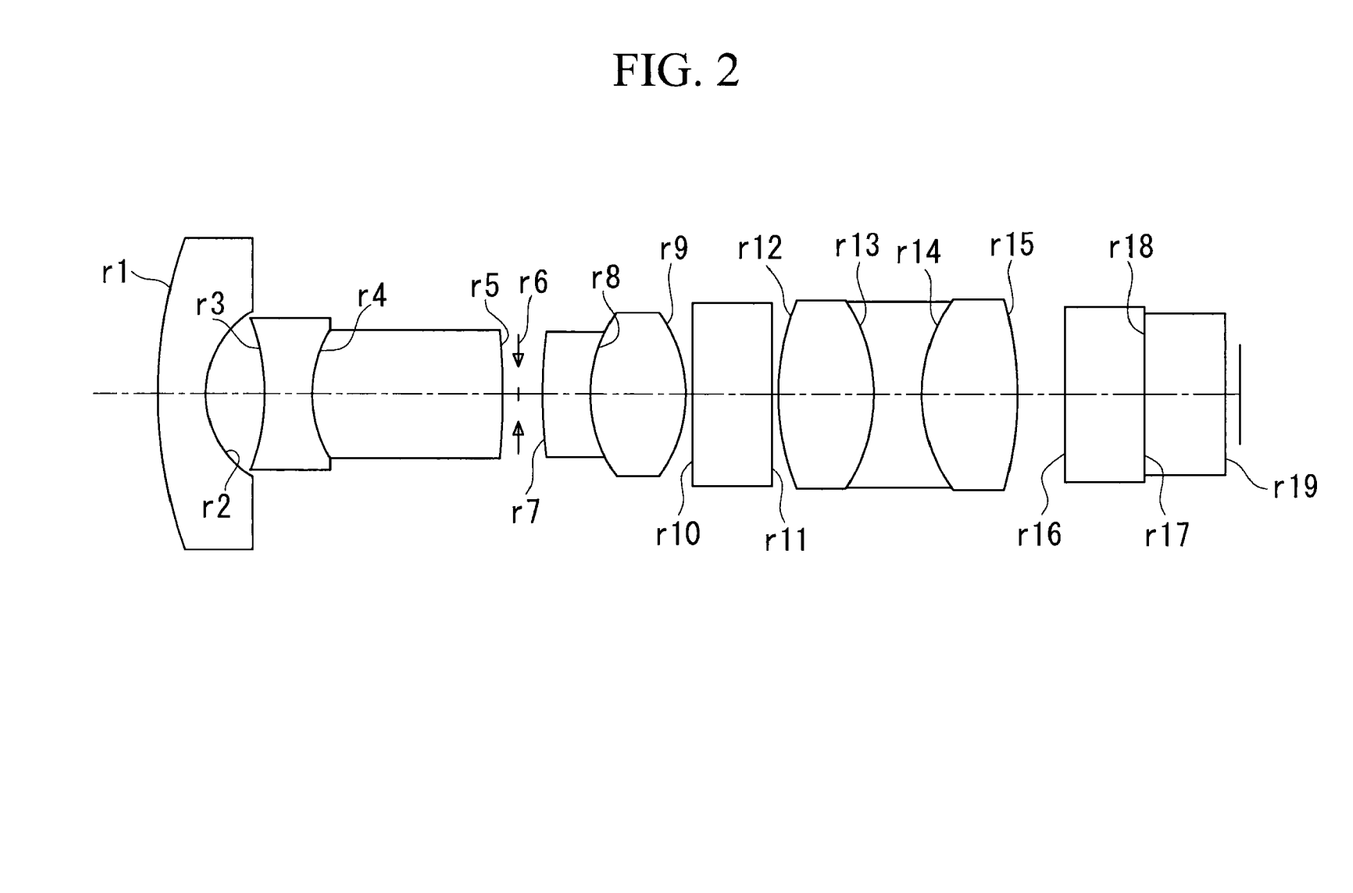
FIG. 2 is a cross-sectional diagram showing an overall configuration of an endoscope objective optical system pertaining to Example 1 of the present invention.
Figure 3:
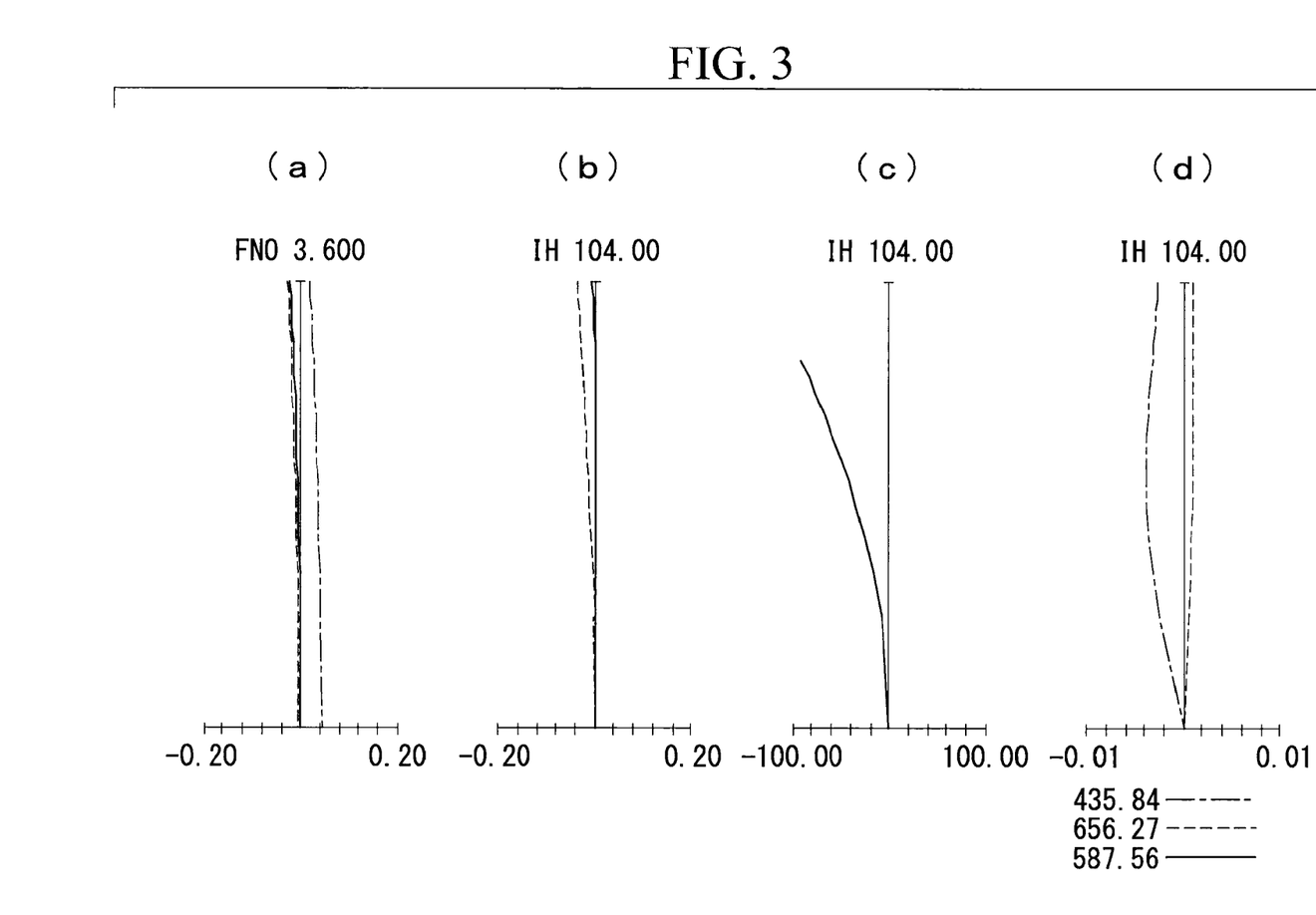
FIG. 3(a) is a graph of an aberration curve showing a spherical aberration of an endoscope illumination optical system of FIG. 2.
FIG. 3(b) is a graph of an aberration curve showing astigmatism thereof.
FIG. 3(c) is a graph of an aberration curve showing distortion thereof.
FIG. 3(d) is a graph of an aberration curve showing a chromatic aberration of magnification thereof.

In FIG. 2, shown is a configuration of an endoscope objective optical system pertaining to Example 1 of the present invention, and lens data thereof is shown below. In addition, in FIG. 3, shown are graphs of aberration curves of the endoscope objective optical system pertaining to the present Example.

Lens Data

| Surface Number | r | d | Nd | Vd |
|---|---|---|---|---|
| 1 | 3.000 | 0.30 | 2.17840 | 33.00 |
| 2 | 0.625 | 0.37 | | |
| 3 | −1.361 | 0.30 | 2.00330 | 28.27 |
| 4 | 0.800 | 1.19 | 1.49700 | 81.54 |
| 5 | −4.996 | 0.10 | | |
| 6 | Brightness Diaphragm | 0.15 | | |
| 7 | 3.347 | 0.30 | 1.88300 | 40.76 |
| 8 | 0.912 | 0.60 | 1.58144 | 40.75 |
| 9 | −0.882 | 0.04 | | |
| 10 | ∞ | 0.50 | 1.51965 | 75.01 |
| 11 | ∞ | 0.04 | | |
| 12 | 1.596 | 0.60 | 1.64769 | 33.79 |
| 13 | −1.125 | 0.30 | 1.92286 | 18.90 |
| 14 | 1.044 | 0.60 | 1.88300 | 40.76 |
| 15 | −2.282 | 0.30 | | |
| 16 | ∞ | 0.50 | 1.51633 | 64.14 |
| 17 | ∞ | 0.00 | 1.51000 | 63.01 |
| 18 | ∞ | 0.50 | 1.51633 | 64.14 |
| 19 | ∞ | | | |

Entire Length (in air) 6.45

Example 2

Figure 4:
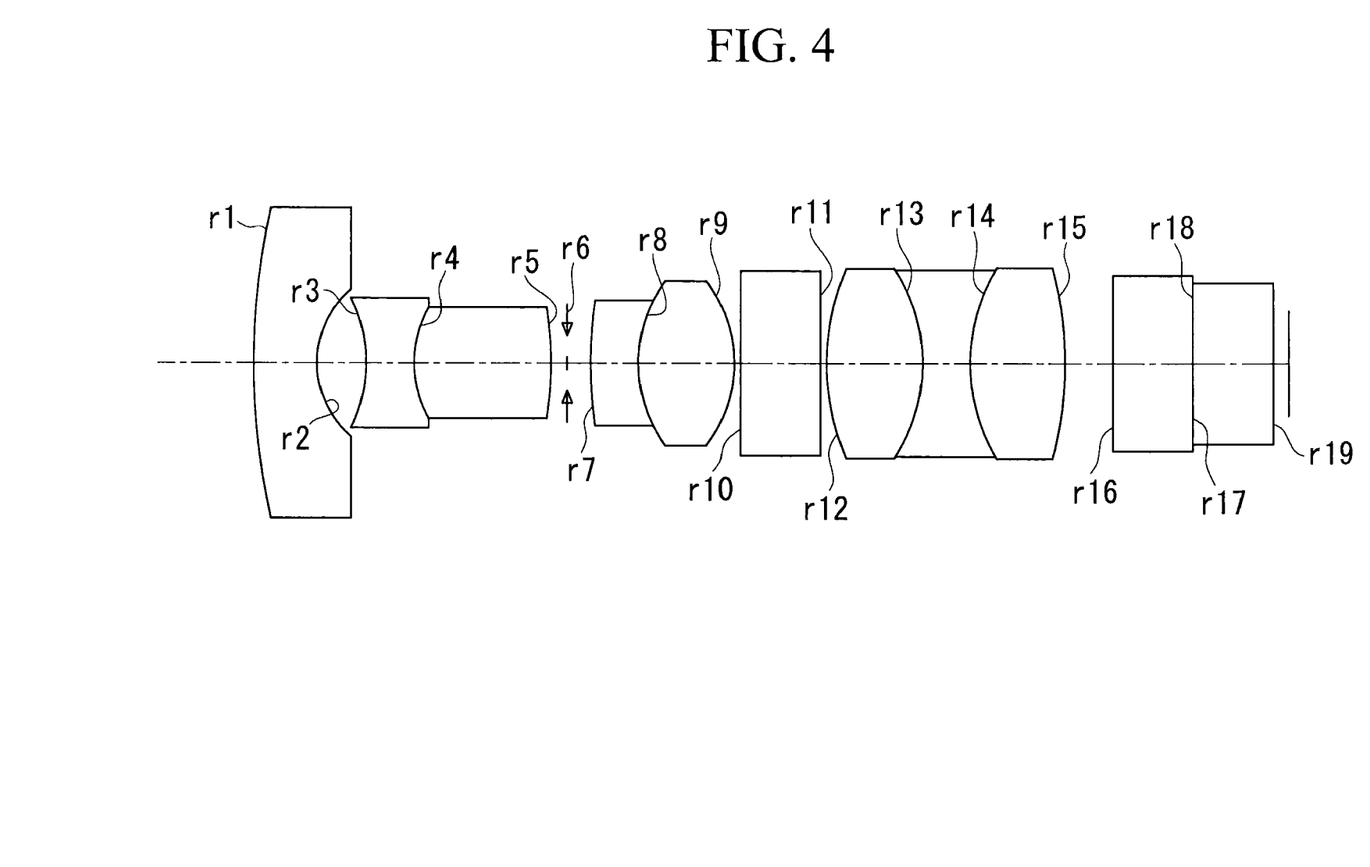
FIG. 4 is a cross-sectional diagram showing an overall configuration of an endoscope objective optical system pertaining to Example 2 of the present invention.
Figure 5:
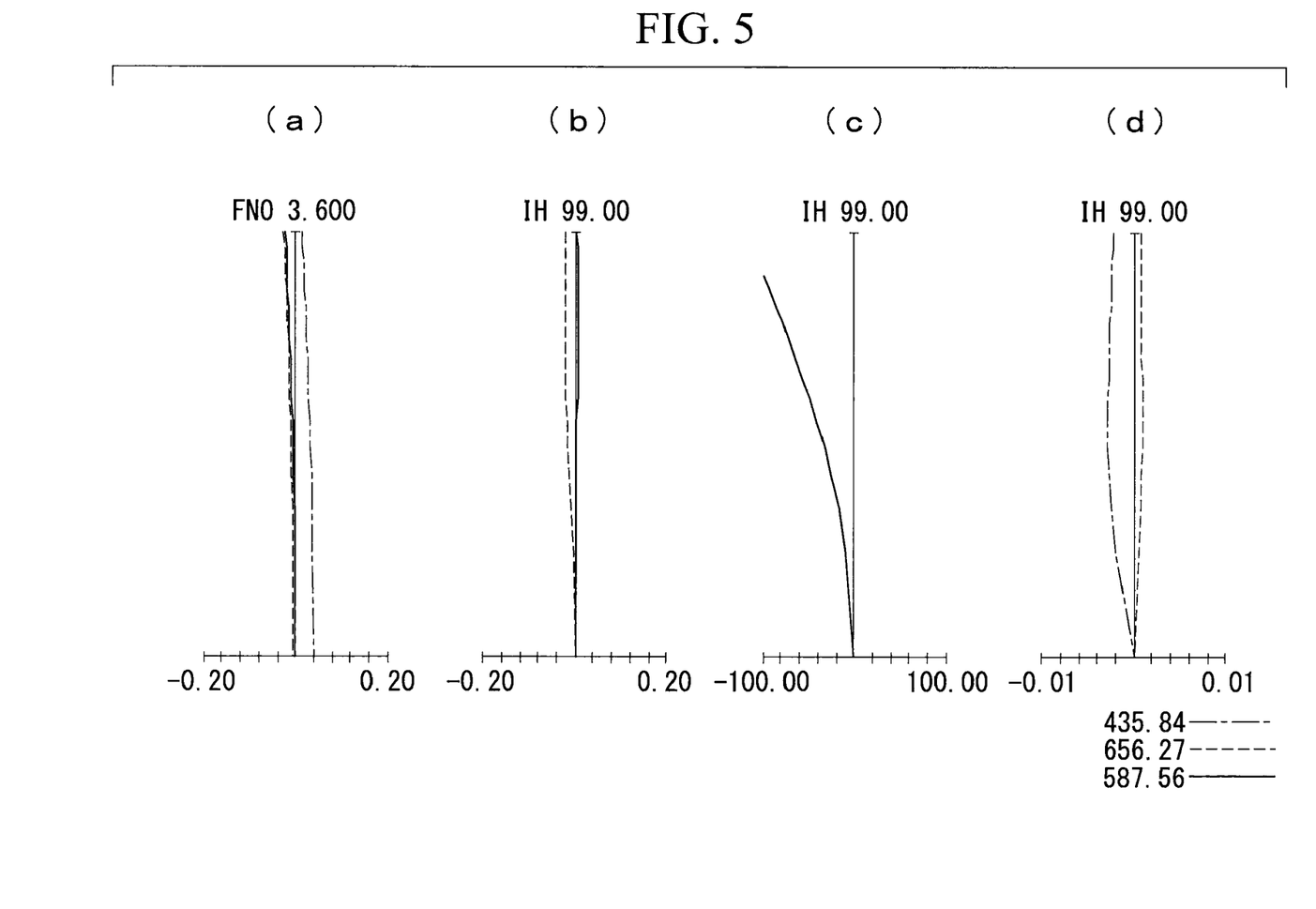
FIG. 5(a) is a graph of an aberration curve showing a spherical aberration of an endoscope illumination optical system of FIG. 4.
FIG. 5(b) is a graph of an aberration curve showing astigmatism thereof.
FIG. 5(c) is a graph of an aberration curve showing distortion thereof.
FIG. 5(d) is a graph of an aberration curve showing a chromatic aberration of magnification thereof.

In FIG. 4, shown is a configuration of an endoscope objective optical system pertaining to Example 2 of the present invention, and lens data thereof is shown below. In addition, in FIG. 5, shown are graphs of aberration curves of the endoscope objective optical system pertaining to the present Example.

Lens Data

| Surface Number | r | d | Nd | Vd |
|---|---|---|---|---|
| 1 | 4.500 | 0.40 | 1.88300 | 40.76 |
| 2 | 0.625 | 0.31 | | |
| 3 | −0.958 | 0.30 | 2.00330 | 28.27 |

-continued

| Surface Number | r | d | Nd | Vd |
|---|---|---|---|---|
| 4 | 0.727 | 0.86 | 1.49700 | 81.54 |
| 5 | -2.236 | 0.10 | | |
| 6 | Brightness Diaphragm | 0.15 | | |
| 7 | 2.811 | 0.30 | 1.88300 | 40.76 |
| 8 | 0.902 | 0.60 | 1.58144 | 40.75 |
| 9 | -0.878 | 0.04 | | |
| 10 | ∞ | 0.50 | 1.51965 | 75.01 |
| 11 | ∞ | 0.04 | | |
| 12 | 1.574 | 0.60 | 1.64769 | 33.79 |
| 13 | -1.125 | 0.30 | 1.92286 | 18.90 |
| 14 | 1.180 | 0.60 | 1.88300 | 40.76 |
| 15 | -2.340 | 0.30 | | |
| 16 | ∞ | 0.50 | 1.51633 | 64.14 |
| 17 | ∞ | 0.00 | 1.51000 | 63.01 |
| 18 | ∞ | 0.50 | 1.51633 | 64.14 |
| 19 | ∞ | | | |

Entire Length (in air) 6.15

Example 3

Figure 6:
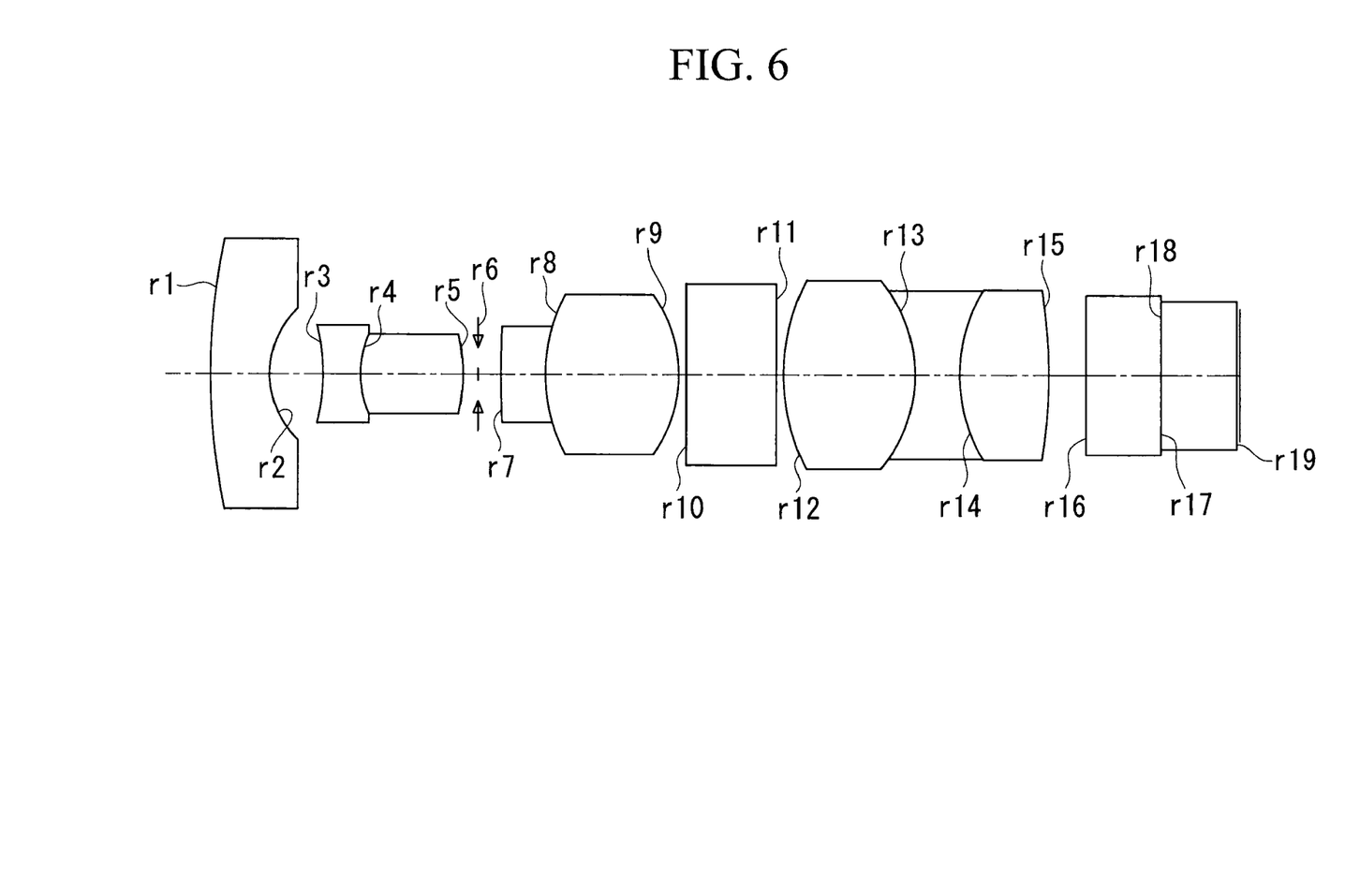
FIG. 6 is a cross-sectional diagram showing an overall configuration of an endoscope objective optical system pertaining to Example 3 of the present invention.
Figure 7:
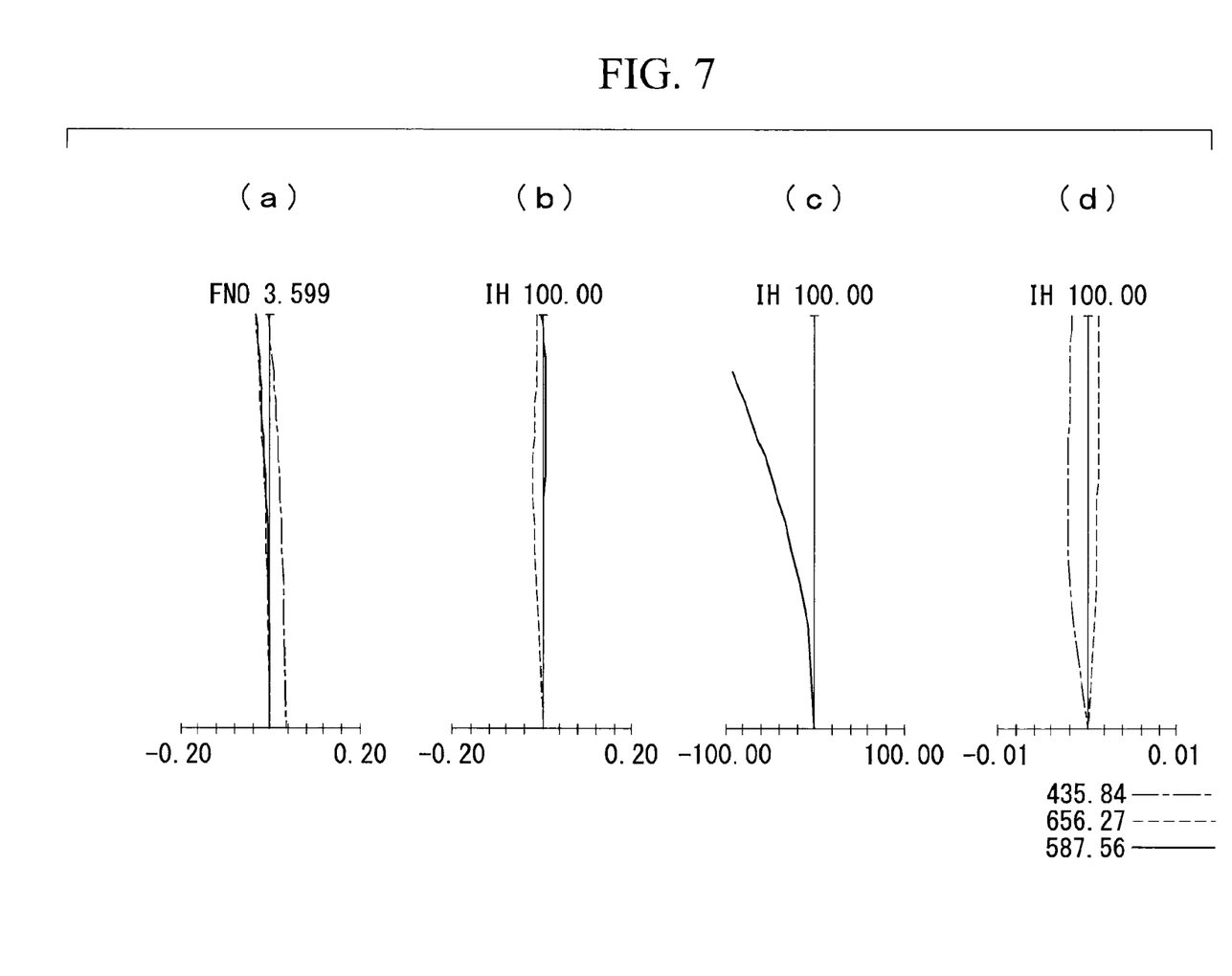
FIG. 7(a) is a graph of an aberration curve showing a spherical aberration of an endoscope illumination optical system of FIG. 6.
FIG. 7(b) is a graph of an aberration curve showing astigmatism thereof.
FIG. 7(c) is a graph of an aberration curve showing distortion thereof.
FIG. 7(d) is a graph of an aberration curve showing a chromatic aberration of magnification thereof.

In FIG. 6, shown is a configuration of an endoscope objective optical system pertaining to Example 3 of the present invention, and lens data thereof is shown below. In addition, in FIG. 7, shown are graphs of aberration curves of the endoscope objective optical system pertaining to the present Example.

Lens Data

| Surface Number | r | d | Nd | Vd |
|---|---|---|---|---|
| 1 | 4.500 | 0.40 | 1.88300 | 40.76 |
| 2 | 0.625 | 0.36 | | |
| 3 | -1.350 | 0.25 | 2.00330 | 28.27 |
| 4 | 0.692 | 0.69 | 1.49700 | 81.54 |
| 5 | -1.207 | 0.10 | | |
| 6 | Brightness Diaphragm | 0.15 | | |
| 7 | 6.094 | 0.30 | 1.88300 | 40.76 |
| 8 | 1.166 | 0.90 | 1.58144 | 40.75 |
| 9 | -0.943 | 0.05 | | |
| 10 | ∞ | 0.60 | 1.51965 | 75.01 |
| 11 | ∞ | 0.05 | | |
| 12 | 1.438 | 0.88 | 1.64769 | 33.79 |
| 13 | -1.015 | 0.30 | 1.92286 | 18.90 |
| 14 | 1.131 | 0.60 | 1.88300 | 40.76 |
| 15 | -3.628 | 0.25 | | |
| 16 | ∞ | 0.50 | 1.51633 | 64.14 |
| 17 | ∞ | 0.01 | 1.51000 | 63.01 |
| 18 | ∞ | 0.50 | 1.51633 | 64.14 |
| 19 | ∞ | | | |

Entire Length (in air) 6.56

Example 4

Figure 8:
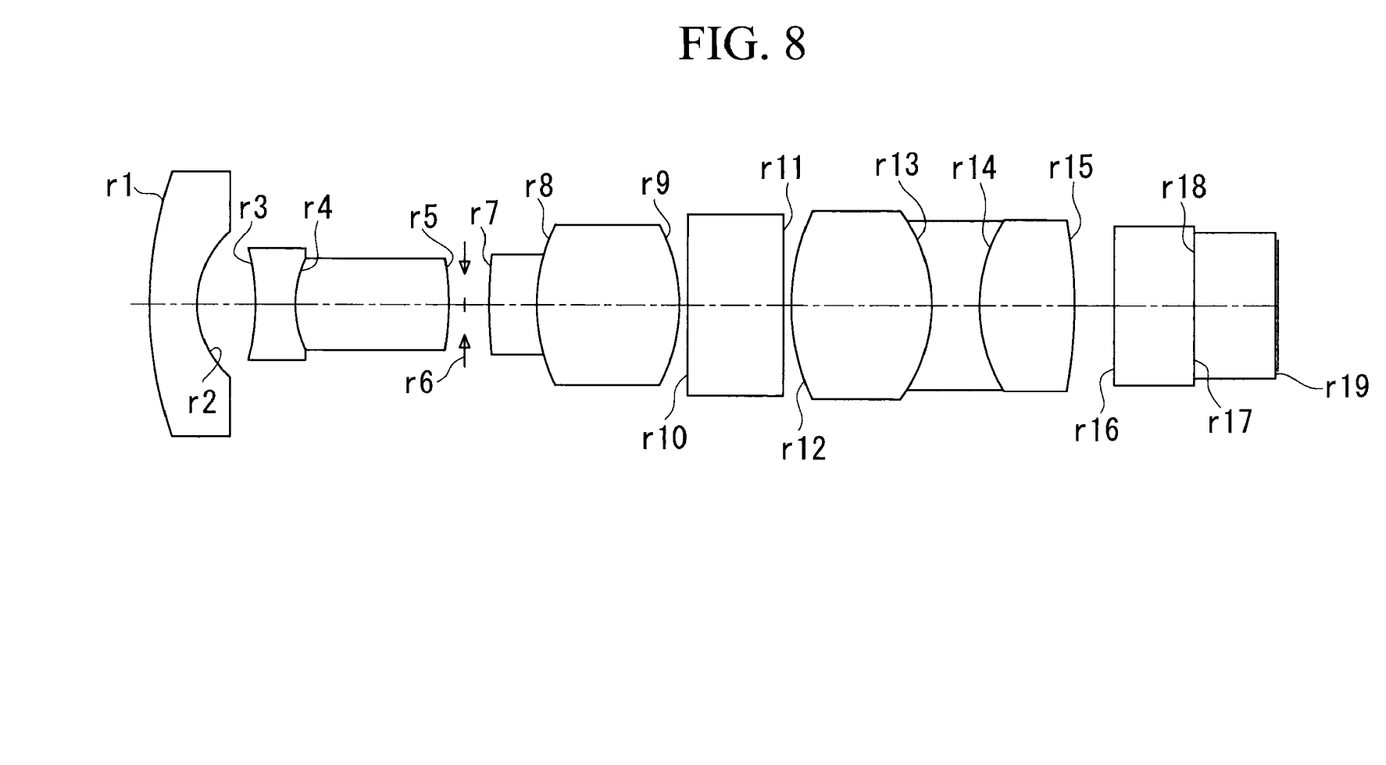
FIG. 8 is a cross-sectional diagram showing an overall configuration of an endoscope objective optical system pertaining to Example 4 of the present invention.
Figure 9:
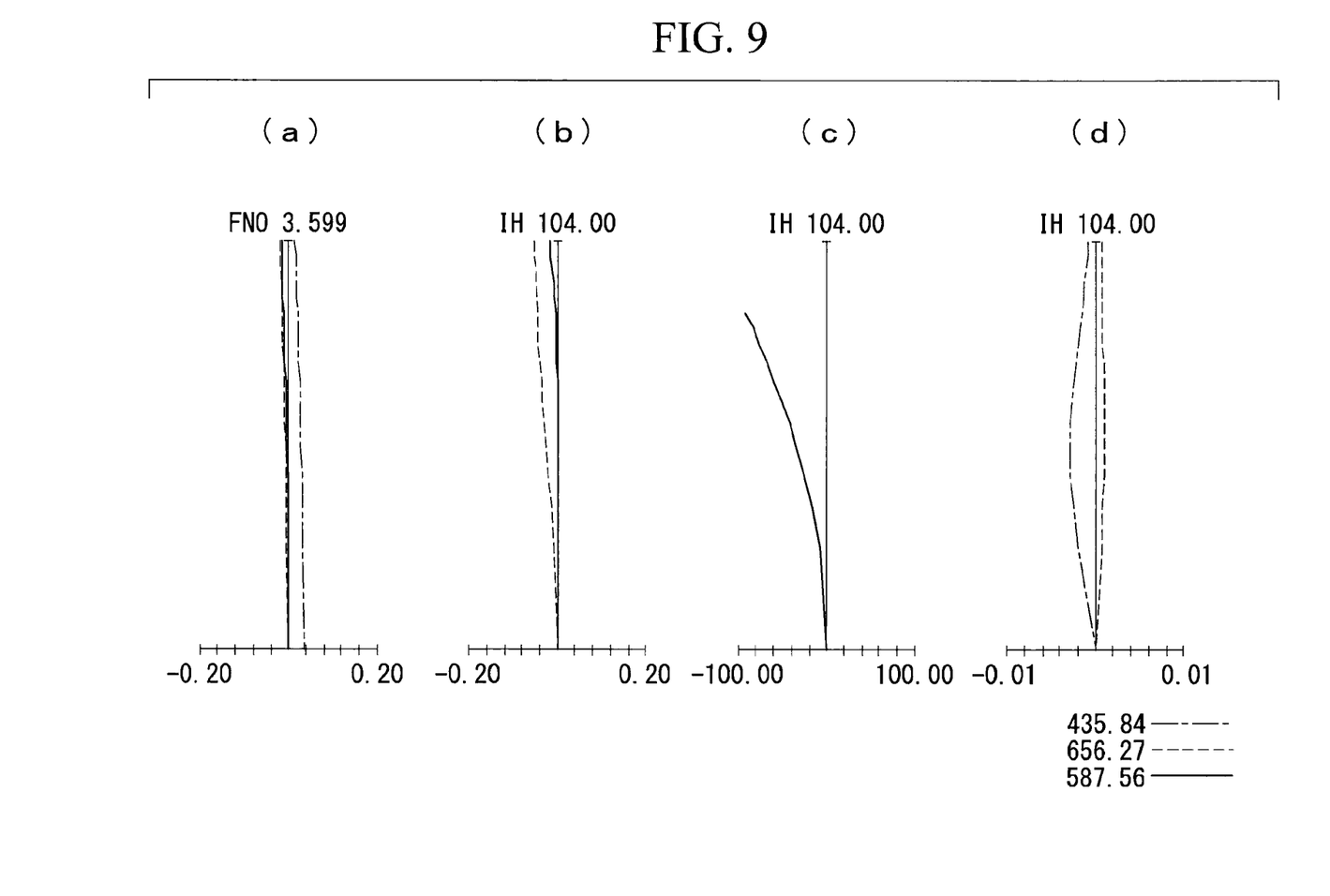
FIG. 9(a) is a graph of an aberration curve showing a spherical aberration of an endoscope illumination optical system of FIG. 8.
FIG. 9(b) is a graph of an aberration curve showing astigmatism thereof.
FIG. 9(c) is a graph of an aberration curve showing distortion thereof.
FIG. 9(d) is a graph of an aberration curve showing a chromatic aberration of magnification thereof.

In FIG. 8, shown is a configuration of an endoscope objective optical system pertaining to Example 4 of the present invention, and lens data thereof is shown below. In addition, in FIG. 9, shown are graphs of aberration curves of the endoscope objective optical system pertaining to the present Example.

Lens Data

| Surface Number | r | d | Nd | Vd |
|---|---|---|---|---|
| 1 | 2.600 | 0.30 | 2.17840 | 33.00 |
| 2 | 0.625 | 0.37 | | |

-continued

| Surface Number | r | d | Nd | Vd |
|---|---|---|---|---|
| 3 | -1.382 | 0.25 | 2.00330 | 28.27 |
| 4 | 0.695 | 0.96 | 1.49700 | 81.54 |
| 5 | -1.796 | 0.10 | | |
| 6 | Brightness Diaphragm | 0.15 | | |
| 7 | 3.068 | 0.30 | 1.88300 | 40.76 |
| 8 | 1.166 | 0.90 | 1.58144 | 40.75 |
| 9 | -1.102 | 0.05 | | |
| 10 | ∞ | 0.60 | 1.51965 | 75.01 |
| 11 | ∞ | 0.05 | | |
| 12 | 1.451 | 0.88 | 1.64769 | 33.79 |
| 13 | -1.015 | 0.30 | 1.92286 | 18.90 |
| 14 | 1.034 | 0.60 | 1.88300 | 40.76 |
| 15 | -3.066 | 0.25 | | |
| 16 | ∞ | 0.50 | 1.51633 | 64.14 |
| 17 | ∞ | 0.01 | 1.51000 | 63.01 |
| 18 | ∞ | 0.50 | 1.51633 | 64.14 |
| 19 | ∞ | | | |

Entire Length (in air) 6.74

It is to be noted that in Table 1, shown are numerical values of the above-described conditional expressions (1) to (6) in the above-described configurations of Examples 1 to 4.

TABLE 1

| | EXAMPLE 1 | EXAMPLE 2 | EXAMPLE 3 | EXAMPLE 4 |
|---|---|---|---|---|
| CONDITIONAL EXPRESSION (1) D3(96deg)/f_a11 | 4.61 | 2.73 | 1.73 | 2.85 |
| CONDITIONAL EXPRESSION (2) (r1 + r2)/r1 − r2) | 1.53 | 1.32 | 1.32 | 1.63 |
| CONDITIONAL EXPRESSION (3) \|v2 − v3\| | 53.3 | 53.3 | 53.3 | 53.3 |
| CONDITIONAL EXPRESSION (4) Nd1 | 2.18 | 1.88 | 1.88 | 2.19 |
| CONDITIONAL EXPRESSION (5) Nd2 | 2 | 2 | 2.01 | 2.01 |
| CONDITIONAL EXPRESSION (6) PW_1/PW_2 | 1.14 | 0.85 | 1.43 | 1.38 |

As mentioned above, according to one aspect of the present invention, since the first lens having negative optical power, the second lens having negative optical power, and the third lens having positive optical power that have been arranged in order from the object side toward the image side are included in a lens group having negative optical power (hereinafter simply referred to as a "negative lens group"), and the endoscope objective optical system includes this negative lens group, the brightness diaphragm, and a lens group having positive optical power (hereinafter referred to as a "positive lens group"), the number of lenses can be reduced, shortening of the entire length and reduction of cost can be achieved, and the diameter of the first lens can be kept small. In addition, the on-axis and off-axis chromatic aberrations can be successfully corrected without using the aspherical lens by using a cemented lens for the positive lens group, and cost can be reduced.

In the above-described aspect, it is preferable to satisfy the following conditional expression (3):

$$51 < |v2-v3| < 60 \quad (3)$$

where, $|v2-v3|$ is the absolute value of the difference between the Abbe numbers of the second and third lenses.

The on-axis and off-axis chromatic aberrations can be successfully corrected by satisfying the above-described conditional expression.

In the above-described aspect, it is preferable to satisfy the following conditional expression (4):

$$1.7 < Nd1 < 2.42 \tag{4}$$

where, Nd1 is a refractive index of a d-line of the first lens.

The refractive index of the first lens can be set to be an appropriate value by satisfying the above-described conditional expression, and even though a curvature of the object side of the negative first lens does not become extremely strong, appropriate negative power can be obtained.

In the above-described aspect, it is preferable to satisfy the following conditional expression (5):

$$1.7 < Nd2 < 2.42 \tag{5}$$

where, Nd2 is a refractive index of a d-line of the second lens.

The refractive index of the second lens can be set to be an appropriate value by satisfying the above-described conditional expression, and even though a curvature of the object side of the negative second lens does not become extremely strong, appropriate negative power can be obtained.

In the above-described aspect, it is preferable that the second and third lenses are joined to each other.

By employing such a manner, the on-axis and off-axis chromatic aberrations can be successfully corrected. In addition, since a lens interval between the negative second lens and the positive third lens can be eliminated, an entrance pupil position can be moved to the object side, and the diameter of the first lens can be kept small.

In the above-described aspect, when optical power of the first lens is represented as PW_f1, and optical power of a cemented lens of the second and third lenses is represented as PW_f2, it is preferable to satisfy the following conditional expression (6):

$$0.3 < PW\_1/PW\_2 < 2.0 \tag{6}$$

Since appropriate power arrangement can be achieved by satisfying the above-described conditional expression, a lens diameter can be kept small while keeping the wide angle of view.

In the above-described aspect, it is preferable that the first lens, the second lens, the third lens, and the positive lens group are all configured with spherical lenses.

By employing such a manner, cost can be reduced.

ADVANTAGEOUS EFFECTS OF INVENTION

According to the present invention, an effect is exerted that the off-axis and on-axis aberrations can be successfully corrected at low cost while having the wide angle of view.

REFERENCE SIGNS LIST

1 Endoscope Objective Optical System
G1 Negative Lens Group
G2 Positive Lens Group
L1 First Lens
L2 Second Lens
L3 Third Lens
L4 Fourth Lens
L5 Fifth Lens
L6 Sixth Lens
L7 Seventh Lens
L8 Eighth Lens
CL1 Cemented lens
CL2 Cemented lens
CL3 Cemented lens
S Brightness Diaphragm
F Plane-parallel Plate
CG Cover Glass

The invention claimed is:

1. An endoscope objective optical system comprising:
a lens group having negative optical power;
a brightness diaphragm; and
a lens group having positive optical power in order from an object side to an image side, wherein
the lens group having negative optical power consists of a first lens having negative optical power, a second lens having negative optical power, and a third lens having positive optical power in order from the object side to the image side,
the second and third lenses are cemented to each other to form a first cemented lens, and wherein
the lens group having positive optical power has a second cemented lens in which at least one positive lens and at least one negative lens have been cemented to each other, and wherein when optical power of the first lens is represented as PW_f1, and combined optical power of the second and third lenses is represented as PW_f2, the following conditional expressions (1), (2), (5)' and (6) are satisfied:

$$1.0 < D3(96\ deg)/f\_all \leq 2.85 \tag{1}$$

$$1.1 < (r1+r2)/(r1-r2) < 5.0 \tag{2}$$

$$1.8 < Nd2 < 2.41 \tag{5)'}$$

$$0.3 < PW\_f1/PW\_f2 < 2.0 \tag{6}$$

where, D3(96 deg) is a distance in which a chief ray of a d-line entering the first lens at an angle of 96 degrees with respect to an optical axis of the objective optical system travels from an object side surface of the third lens to an image side surface of the third lens along the optical axis, and f_all is a focal distance of the whole system,
r1 is a radius of curvature of an object side surface of the first lens,
r2 is a radius of curvature of an image side surface of the second lens, and
Nd2 is a refractive index of a d-line of the second lens.

2. The endoscope objective optical system according to claim 1, satisfying the following conditional expression (3):

$$51 < |\upsilon2-\upsilon3| < 60 \tag{3}$$

where, $|\upsilon2-\upsilon3|$ is an absolute value of a difference between Abbe numbers of the second and third lenses.

3. The endoscope objective optical system according to claim 1, satisfying the following conditional expression (4):

$$1.7 < Nd1 < 2.42 \tag{4}$$

where, Nd1 is a refractive index of the d-line of the first lens.

4. The endoscope objective optical system according to claim 1, wherein all of the first lens, the second lens, the third lens, and lenses forming the lens group having positive optical power are configured only with spherical lenses.

* * * * *